United States Patent
Levin et al.

(10) Patent No.: US 8,016,810 B2
(45) Date of Patent: Sep. 13, 2011

(54) TRANSDERMAL DELIVERY SYSTEM FOR COSMETIC AGENTS

(75) Inventors: Galit Levin, Nordiya (IL); Hagit Sacks, Modi'in (IL); Sergey Rudaev, Ariel (IL)

(73) Assignee: TransPharma Medical Ltd., Lod (IL)

( * ) Notice: Subject to any disclaimer, the term of this patent is extended or adjusted under 35 U.S.C. 154(b) by 38 days.

(21) Appl. No.: 10/561,933

(22) PCT Filed: Jun. 23, 2004
(Under 37 CFR 1.47)

(86) PCT No.: PCT/IL2004/000561
§ 371 (c)(1),
(2), (4) Date: Mar. 27, 2007

(87) PCT Pub. No.: WO2004/112689
PCT Pub. Date: Dec. 29, 2004

(65) Prior Publication Data
US 2007/0270732 A1    Nov. 22, 2007

Related U.S. Application Data

(60) Provisional application No. 60/480,229, filed on Jun. 23, 2003.

(51) Int. Cl.
*A61M 31/00* (2006.01)
(52) U.S. Cl. ............ 604/501; 604/20; 424/449
(58) Field of Classification Search ........... 604/20, 604/22, 890.1, 501; 424/449
See application file for complete search history.

(56) References Cited

U.S. PATENT DOCUMENTS

| | | | |
|---|---|---|---|
| 4,536,399 A | 8/1985 | Flynn | 514/63 |
| 4,545,990 A | 10/1985 | Le Foyer de Costil | 514/557 |
| 4,588,724 A | 5/1986 | Greenway | 514/250 |
| 4,603,146 A | 7/1986 | Kligman | 514/559 |
| 4,608,370 A | 8/1986 | Aronsohn | 514/159 |
| 4,613,592 A | 9/1986 | Benzoni | 514/63 |
| 4,767,750 A | 8/1988 | Jacquet | 514/159 |
| 4,795,638 A | 1/1989 | Ayache | 424/195.1 |
| 4,880,621 A | 11/1989 | Grollier | 424/74 |
| 4,933,177 A | 6/1990 | Grollier | 424/74 |
| 5,051,449 A | 9/1991 | Kligman | 514/559 |
| 5,057,502 A | 10/1991 | Walsh | 514/54 |
| 5,116,605 A | 5/1992 | Alt | 424/70 |

(Continued)

FOREIGN PATENT DOCUMENTS

JP    11-130680    5/1999

(Continued)

OTHER PUBLICATIONS

Bramson, J., et.al. "Enabling topical immunization via microporation: a novel method for pain-free and needle-free delivery of adenovirus-based vaccines." Gene Therapy. Feb. 2003; 10(3): 251-260.*

(Continued)

*Primary Examiner* — Theodore Stigell
*Assistant Examiner* — Brandy C Scott
(74) *Attorney, Agent, or Firm* — Winston & Strawn LLP

(57) ABSTRACT

An intradermal or transdermal delivery system for topical administration of cosmetic agents, particularly water-soluble, poorly water-soluble, or water-insoluble cosmetic agents, in conjunction with an apparatus that generates micro-channels in the skin of a subject, is useful in treating skin conditions such as cellulite, hyper-pigmentation, skin aging, and acne.

11 Claims, 8 Drawing Sheets

U.S. PATENT DOCUMENTS

| | | | | |
|---|---|---|---|---|
| 5,194,259 | A | 3/1993 | Soudant | 424/401 |
| 5,215,759 | A | 6/1993 | Mausner | 424/489 |
| 5,352,438 | A | 10/1994 | N'Guyen | 424/45 |
| 5,362,494 | A | 11/1994 | Zysman | 424/401 |
| 5,445,822 | A | 8/1995 | Bracco | 424/401 |
| 5,482,710 | A | 1/1996 | Slavtcheff | 424/195.1 |
| 5,523,090 | A | 6/1996 | Znaiden | 424/401 |
| 5,637,316 | A | 6/1997 | Ribier | 424/450 |
| 5,679,374 | A | 10/1997 | Fanchon | 424/450 |
| 5,690,947 | A | 11/1997 | Habif | 424/401 |
| 5,814,322 | A | 9/1998 | Sebillotte-Arnaud | 424/401 |
| 5,843,476 | A | 12/1998 | Ribier | 424/450 |
| 5,885,211 | A | 3/1999 | Eppstein et al. | 600/309 |
| 5,889,062 | A | 3/1999 | Hoppe | 514/690 |
| 5,910,490 | A | 6/1999 | Moczar | 514/54 |
| 5,961,999 | A | 10/1999 | Bimczok | 424/401 |
| 5,962,482 | A | 10/1999 | Bissett | 514/356 |
| 5,983,130 | A | 11/1999 | Phipps et al. | 604/20 |
| 6,022,316 | A | 2/2000 | Eppstein et al. | 600/309 |
| 6,071,526 | A | 6/2000 | Schmidt | 424/401 |
| 6,142,939 | A | 11/2000 | Eppstein et al. | 600/309 |
| 6,148,232 | A * | 11/2000 | Avrahami | 604/20 |
| 6,159,194 | A | 12/2000 | Eggers | 604/500 |
| 6,169,920 | B1 | 1/2001 | Haak et al. | 604/20 |
| 6,173,202 | B1 | 1/2001 | Eppstein | 604/20 |
| 6,302,874 | B1 * | 10/2001 | Zhang et al. | 604/522 |
| 6,317,629 | B1 | 11/2001 | Haak et al. | 604/20 |
| 6,365,137 | B1 | 4/2002 | Aust | 424/62 |
| 6,417,226 | B1 | 7/2002 | Perricone | 514/474 |
| 6,477,410 | B1 * | 11/2002 | Henley et al. | 604/20 |
| 6,527,716 | B1 | 3/2003 | Eppstein | 600/309 |
| 6,562,353 | B1 | 5/2003 | Breton | 424/401 |
| 6,597,946 | B2 | 7/2003 | Avrahami et al. | 604/20 |
| 6,611,706 | B2 | 8/2003 | Avrahami et al. | 604/20 |
| 6,615,079 | B1 | 9/2003 | Avrahami | 604/20 |
| 6,708,060 | B1 | 3/2004 | Avrahami et al. | 604/20 |
| 6,711,435 | B2 | 3/2004 | Avrahami | 604/20 |
| 6,718,201 | B1 | 4/2004 | Phipps et al. | 604/20 |
| 6,947,791 | B2 | 9/2005 | Zhang | 604/20 |
| 2002/0010414 | A1 * | 1/2002 | Coston et al. | 604/20 |
| 2002/0038101 | A1 * | 3/2002 | Avrahami et al. | 604/20 |
| 2002/0161324 | A1 * | 10/2002 | Henley et al. | 604/20 |
| 2002/0165481 | A1 | 11/2002 | Hofmann et al. | 604/20 |
| 2002/0198484 | A1 | 12/2002 | Young et al. | 604/20 |
| 2003/0073949 | A1 | 4/2003 | Giammarusti | 604/20 |
| 2003/0199808 | A1 * | 10/2003 | Henley et al. | 604/20 |
| 2004/0022753 | A1 | 2/2004 | Shin | 424/449 |

FOREIGN PATENT DOCUMENTS

| | | |
|---|---|---|
| JP | 2003-063997 | 3/2003 |
| WO | WO 2004/039426 A3 | 5/2004 |
| WO | WO 2004/039427 A3 | 5/2004 |
| WO | WO 2004/039428 A3 | 5/2004 |

OTHER PUBLICATIONS

Sintov, A.C., et.al. "Radiofrequency-driven skin microchanneling as a new way for electrically assisted transdermal delivery of hydrophilic drugs." Journal of Controlled Release. vol. 89, Issue 2, Apr. 2003, p. 311-320.*

Dayan, Nava and Touitou, Elka (2000) Carriers for Skin Delivery of Trihexyphnidyl HC1: Ethosomes vs. Liposomes, Biomaterials 21(8):1879-85.

* cited by examiner

TRANSDERMAL DELIVERY SYSTEM FOR COSMETIC AGENTS

CROSS REFERENCE TO RELATED APPLICATIONS

This application is a 371 filing of international application PCT/IL2004/000561 filed Jun. 23, 2004 and published in English as WO 2004/112689 A2 on Dec. 29, 2004 and claims priority of U.S. provisional application 60/480,299 filed on Jun. 23, 2003, which applications are hereby incorporated by reference herein in their entirety.

FIELD OF THE INVENTION

The present invention relates to an intradermal or transdermal delivery system for effective topical administration of cosmetic agents, unexpectedly useful for all types of cosmetic agents including water soluble, poorly soluble, or insoluble cosmetic agents, in conjunction with an apparatus that generates micro-channels in the skin of a subject. The intradermal or transdermal delivery system enhances the efficacy of cosmetic agents thus improves the appearance of skin.

BACKGROUND OF THE INVENTION

The skin is a complex structure that functions as a barrier to ingress of foreign substances into the body. Molecules moving from the environment into and through an intact skin must first penetrate the stratum corneum, which acts as highly resistant lipid barrier to penetration of these molecules into the skin. In both the pharmaceutical and cosmetic fields, significant efforts have been put forth in attempts to overcome the barrier of the stratum corneum in order to deliver topically functional agents into the skin. Generally, three primary routes across the stratum corneum are available for molecular transport: (1) Normal or chemically modified skin allows diffusion of small molecules, usually following a tortuous intercellular path within the lipids of the stratum corneum; (2) "Shunt" pathways through the hair follicles and sweat ducts may be utilized during iontophoresis, pressure-mediated delivery, and liposomal transport; and (3) Transcellular pathways crossing both the cells and intercellular lipids of the stratum corneum can be created by electroporation to allow passage of chemical compounds The technique of iontophoresis is in wide use in the administration of drugs as it effectively delivers electrically charged medicaments through the skin and into the capillary structure and lymphatic system. This technique avoids the gastrointestinal side effects sometimes associated with orally ingested drugs and is preferable to subcutaneous or intramuscular injection because of its relatively benign and painless nature.

Although the iontophoresis has been found to be effective, it is also known to be accompanied by a number of undesirable side effects, such as the occurrence of skin injury in the form of iontophoretic burns and irritation in the treated area as well as the formation of undesirable vesicles and bullae on the skin in the treated area. Various complicated methods for preventing these iontophoretic burns have been developed. However, such methods and apparatus have generally been found not to be adequately effective. Consequently, iontophoretic treatments have usually been limited to relatively low electrical currents and relatively short periods of administration.

Iontophoretic drug delivery systems have also been primarily limited to delivering a drug of only a single polarity at a time to a given area, at relatively low concentrations, and have not been suitable for simultaneous delivery of multiple drugs.

The other technique, electroporation, facilitates the transdermal or intradermal delivery of uncharged substances by electrically inducing the formation of transient dermal micropores that allow mobilization of the uncharged substances by diffusion. However, electroporation generally does not produce pores of sufficient diameter to allow passage of large molecules.

Iontophoresis as well as electroporation have been incorporated into many transdermal delivery devices including dermal patches and bioelectrodes. For example, there are many dermal patches known today that incorporate a power source and electrical circuitry for facilitating transdermal delivery. However, these iontophoretic dermal patches and bioelectrodes are often expensive and must be handled by a clinician.

Electrotransport or iontophoretic drug delivery devices have been disclosed as being useful for the delivery of many types of drugs for which it is anticipated that transdermal delivery would be advantageous. U.S. Pat. Nos. 6,169,920 and 6,317,629 to Alza, for example, disclose iontophoretic drug delivery apparatus, and U.S. Pat. Nos. 5,983,130 and 6,718,201 to Alza discloses an electrotransport agent delivery method and apparatus mostly suitable for charged but also for uncharged drugs.

U.S. Pat. Nos. 5,885,211; 6,022,316; 6,142,939; 6,173,202; and 6,527,716 to Eppstein et al., describe devices and methods for forming micropores in the stratum corneum by heating tissue-bound water above the vapor point with a heat conducting element so as to enhance transdermal transport of an analyte or active substance. Additional enhancement techniques include the use of sonic energy, pressure, and chemical enhancers.

Electrosurgery techniques have been used to contract collagen fibers in soft tissue. These techniques typically involve the application of radio frequency (RF) energy to soft collagen tissue to contract and restrict the tissue elasticity. U.S. Pat. No. 6,159,194 to Eggers et al., describes electrosurgical apparatus and methods for inducing tissue contraction while limiting the thermal damage to tissue adjacent to and underlying the treatment site.

U.S. Pat. No. 6,148,232 to Avrahami, which is incorporated herein by reference, describes a device for ablating the stratum corneum of a subject. The device includes a plurality of electrodes, which are applied at respective points on skin of a subject. A power source applies electrical energy between two or more of the electrodes to cause ablation of distinct regions of the stratum corneum (SC), primarily beneath the respective electrodes, and to generate micro-channels. Various techniques for limiting ablation to the stratum corneum are described, including spacing of the electrodes and monitoring the electrical resistance of skin between adjacent electrodes. U.S. Pat. Nos. 6,597,946; 6,611,706; 6,708,060; and 6,711,435 to Avrahami, all assigned to the applicant of the present application and incorporated herein by reference, disclose additional devices for ablating the stratum corneum and generating micro-channels so as to facilitate transdermal passage of substances through the skin. The devices are aimed at reducing sensation and minimizing damage to skin underlying the stratum corneum during micro-channel generation.

WO 2004/039426; WO 2004/039427; and WO 2004/039428, all assigned to the applicant of the present application and incorporated herein by reference, disclose systems and methods for transdermal delivery of pharmaceutical agents. Specifically disclosed are hydrophilic anti-emetic agents, therapeutic agents from patches comprising dried compositions, and pharmaceutical compositions comprising water-insoluble drugs and carrier molecules, which enhance the solubility of the drugs in aqueous solutions.

There is still a recognized need for, and it would be highly advantageous to have a system and methods for efficient intradermal or transdermal delivery of cosmetic agents, which enhance the penetration of the cosmetic agents into skin and increase their bioavailability. As many chemical agents useful for treating skin conditions have limited efficacy due to their poor solubility in aqueous-based cosmetic compositions or to significant oxidation, and as skin is a barrier normally impermeable to water soluble or hydrophilic agents, there is still an unmet need for a system and methods for administering cosmetic agents, which system and methods overcome the major drawbacks of the presently known treatments and improve dramatically the efficacy of cosmetic agents.

SUMMARY OF THE INVENTION

The present invention provides an effective system for intradermal or transdermal delivery of cosmetic agents. Particularly, the present invention provides a system and methods for intradermal or transdermal delivery of water soluble, poorly soluble, or insoluble cosmetic agents.

The present invention utilizes an intradermal or transdermal delivery system that does not require permeation enhancers as compared to methods known in the art, thereby achieves the desired cosmetic benefits without causing skin damage and without using harsh chemicals that may detract from the appearance of the skin.

In one aspect, the present invention provides a system for intradermal or transdermal delivery of a cosmetic agent, unexpectedly effective for water soluble, poorly soluble, or water-insoluble, comprising: an apparatus for facilitating intradermal or transdermal delivery of a cosmetic agent through skin of a subject, the apparatus capable of generating at least one micro-channel in a region on the skin of the subject, and a cosmetic or dermatological composition comprising a dermatologically effective amount of at least one water soluble, poorly soluble or water-insoluble cosmetic agent and a cosmetically or dermatologically acceptable carrier.

The terms "transdermal" or "intradermal" delivery as used herein refer to the site of delivery of a cosmetic agent. Thus, the desired delivery may be intradermal to treat conditions of the dermal layers beneath the stratum corneum or it may be transdermal to deliver agents intended to affect subcutaneous layers.

The term "micro-channel" as used in the context of the present application refers to a pathway, generally extending from the surface of the skin through all or significant part of the stratum corneum, through which molecules can diffuse. The terms "micropore" and "micro-channels" are used herein interchangeably.

According to some embodiments, the present invention incorporates the techniques for creating micro-channels by inducing ablation of the stratum corneum using electrical energy including the devices disclosed in the following U.S. Pat. Nos. 6,148,232; 6,597,946; 6,611,706; 6,711,435; 6,708,060; and 6,615,079; the contents of which are incorporated herein in their entirety by reference. It is however emphasized that although some preferred embodiments of the present invention relate to intradermal or transdermal delivery obtained by ablating the skin by the aforementioned apparatus, substantially any method known in the art for generating micro-channels in the skin of a subject may be used.

According to one embodiment of the present invention, the system comprises an apparatus for facilitating intradermal or transdermal delivery of a cosmetic agent through skin of a subject, said apparatus comprising:
 a. an electrode cartridge comprising a plurality of electrodes;
 b. a main unit comprising a control unit which is adapted to apply electrical energy between two or more electrodes when the electrodes are in vicinity of the skin, typically generating current flow or one or more sparks, enabling ablation of stratum corneum in a region beneath the electrodes, thereby generating at least one micro-channel.

According to another embodiment of the invention, the control unit of the apparatus comprises circuitry to control the magnitude, frequency, and/or duration of the electrical energy delivered to the electrodes, so as to control the current flow or spark generation, and thus the width, depth and shape of the one or more formed micro-channels. Preferably, the electrical energy is at radio frequency.

According to a currently preferred embodiment, the electrode cartridge comprising a plurality of electrodes generates a plurality of micro-channels having uniform shape and dimensions. Preferably, the electrode cartridge is removable. More preferably, the electrode cartridge is discarded after one use, and as such it is designed for easy attachment to the main unit and subsequent detachment from the main unit.

It will be appreciated that the delivery of electrical energy to the skin may have beneficial effects on the appearance of skin even without administering a cosmetic agent as the electrical energy may facilitate removing of dead keratinized cells.

According to the principles of the invention, the system for intradermal or transdermal delivery of a cosmetic agent comprises a cosmetic or dermatological composition comprising a dermatologically effective amount of at least one water soluble, poorly water-soluble, or water-insoluble cosmetic agent and a cosmetically or dermatologically acceptable carrier. Typically, the cosmetic composition is placed over the region in which micro-channels are present so as to improve the condition of the subject's skin in that region.

The term "water-soluble" cosmetic agent as used herein refers to a compound that typically has solubility in water in the range of 1 gr/ml to 1 gr/30 ml at room temperature. The term "poorly water-soluble" cosmetic agent as used herein refers to a compound that typically has solubility in water in the range of 1 gr/30 ml to 1 gr/10,000 ml at room temperature. The term "water-insoluble" cosmetic agent as used herein refers to a compound that typically has solubility in water of less that 1 gr/10,000 ml at room temperature. The present invention encompasses water-soluble cosmetic agents, poorly water-soluble cosmetic agents, and water-insoluble cosmetic agents.

Examples of the cosmetic agents that may be used according to the present invention include, but are not limited to, xanthines, retinoids, α-hydroxy acids, β-hydroxy acids, α-2 adrenergic inhibitors, β-adrenergic agonists, aromatase inhibitors, anti-estrogens, hydroquinone, ascorbic acid, kojic acid, corticosteroids, mucopolysaccharides, collagen, estrogens, isoflavonoids, cinnamic acid, benzoyl peroxide, tropolone, catechol, mercaptoamine, niacinamide, tocopherol, ferulic acid, azelaic acid, botulinum, urea, a derivative or salt thereof. In a currently preferred embodiment, the cosmetic agent is selected from caffeine, salicylic acid, and hydroquinone.

The composition may be formulated into anhydrous compositions, aqueous solutions or suspensions, oil-in-water or water-in-oil emulsions such as macroemulsions, microemulsions or nanoemulsions, oily droplets in aqueous solutions, micelles, liposomes, ethosomes, aqueous suspensions of nanoparticles or any other known cosmetic formulation. The composition may be in a form of a gel, paste, cream, foam, spray, skin patch, stick, or any other form as known in the art.

According to another aspect, the present invention provides a method for treating a skin condition in a subject, said method comprising the steps of:

(i) generating at least one micro-channel in a region of skin of a subject suffering from a skin condition; and (ii) topically applying a cosmetic or dermatological composition comprising a dermatologically effective amount of at least one water-soluble, poorly water-soluble, or water-insoluble cosmetic agent and a cosmetically or dermatologically acceptable carrier to the region of the skin in which the micro-channels are present so as to improve the skin condition of said subject.

According to one embodiment, generating micro-channel in the skin of a subject is performed by ablation of the skin, preferably by the techniques and devices described hereinabove. Preferably, a plurality of micro-channels is generated.

According to a further embodiment, skin conditions that may be treated by the method of the invention include, but are not limited to, cellulite, acne vulgaris, acne cystic, skin aging, skin wrinckles, hyperpigmentation including discrete and mottled hyperpigmentation, keratosis including actinic, solar and sebhorratic keratosis, skin blemish, dandruff, warts, photodamaged skin, chronic dermatoses such as psoriasis, dermatitis including atopic dermatitis and seborrheic dermatitis, dryness, ichthyosis, and other types of viral, fungal or bacterial skin infections.

According to another embodiment, the cosmetic agent is selected from the group consisting of xanthines, retinoids, α-hydroxy acids, β-hydroxy acids, α-2 adrenergic inhibitors, β-adrenergic agonists, aromatase inhibitors, anti-estrogens, hydroquinone, ascorbic acid, kojic acid, corticosteroids, mucopolysaccharides, collagen, estrogens, isoflavonoids, cinnamic acid, benzoyl peroxide, tropolone, catechol, mercaptoamine, niacinamide, tocopherol, ferulic acid, azelaic acid, botulinum, urea, a derivative, or salt thereof. In a currently preferred embodiment, the cosmetic agent is selected from caffeine, salicylic acid, and hydroquinone.

These and other embodiments of the present invention will be better understood in relation to the figures, description, examples, and claims that follow.

DETAILED DESCRIPTION OF THE INVENTION

Figure 1:
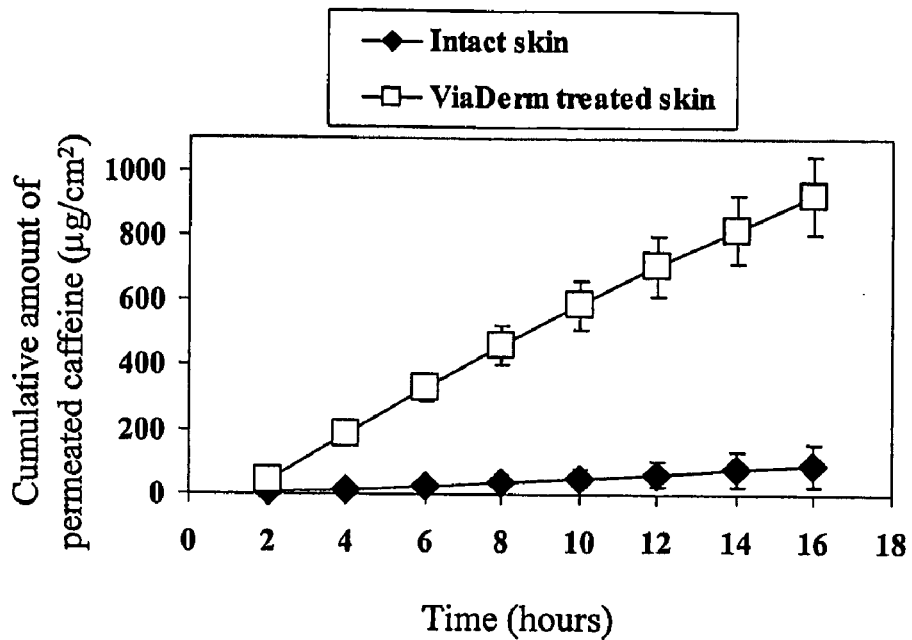
FIG. 1 shows permeation assay of caffeine from an aqueous solution through porcine ear skin in which skin micro-channels were generated compared to intact skin.

The present invention provides a system for an effective intradermal or transdermal delivery of cosmetic agents including water-soluble cosmetic agents on one hand, and poorly water-soluble or water-insoluble cosmetic agents, on the other hand.

According to one aspect, the present invention provides a system for intradermal or transdermal delivery of a cosmetic agent comprising: an apparatus for facilitating intradermal or transdermal delivery of a cosmetic agent through skin of a subject, the apparatus capable of generating at least one micro-channel in a region on the skin of the subject, and a cosmetic or dermatological composition comprising a dermatologically effective amount of at least one water-soluble, poorly water-soluble, or water insoluble cosmetic agent and a cosmetically or dermatologically acceptable carrier.

The terms "transdermal" or "intradermal" delivery as used herein refer to the site of delivery of a cosmetic agent. Thus, the desired delivery may be intradermal to treat conditions of the dermal layers beneath the stratum corneum, e.g., the dermal melanocytes in skin whitening or the dermal sebaceous glands in acne, or may be transdermal to deliver agents intended to affect subcutaneous layers, e.g., subdermal adipose cells in cellulite.

The term "micro-channel" as used in the context of the present application refers to a pathway generally extending from the surface of the skin through all or a significant part of the stratum corneum, through which molecules can diffuse. The terms "micropore" and "micro-channels" are used herein interchangeably.

The term "water-soluble" cosmetic agent as used herein refers to a compound that typically has solubility in water in the range of 1 gr/ml to 1 gr/30 ml at room temperature. The term "poorly water-soluble" cosmetic agent as used herein refers to a compound that typically has solubility in water in the range of 1 gr/30 ml to 1 gr/10,000 ml at room temperature. The term "water-insoluble" cosmetic agent as used herein refers to a compound that typically has solubility in water of less that 1 gr/10,000 ml at room temperature. The present invention encompasses water-soluble cosmetic agents, poorly water-soluble cosmetic agents, and water-insoluble cosmetic agents.

The term "cosmetic" agent refers to an agent that is suitable for administration to skin and is capable of improving the appearance of skin such as, for example, reducing or eliminating hyperpigmentation, reducing or eliminating acne, or reducing or eliminating cellulite. The terms "cosmetic" and "dermatological" agent or composition are used interchangeably herein throughout the specification and claims.

Unexpectedly, it is now disclosed that the system of the present invention achieves highly efficient permeation of cosmetic agents through skin. The permeation efficacy of the cosmetic agents was higher in skin in which micro-channels were generated as compared to intact skin. The principles of the invention are particularly exemplified herein below using hydroquinone (water-soluble agent; solubility of 1 gr/14 ml water at 22° C.), caffeine (poorly water-soluble agent; solubility of 1 gr/46 ml water at 22° C.), and salicylic acids (poorly water-soluble agent; solubility of 1 gr/500 ml water at 22° C.). However, it will be understood that the compositions and methods of the invention are applicable to a wide variety of water-soluble, poorly water-soluble, and water-insoluble cosmetic agents as listed herein below.

Generation of micro-channels through the stratum corneum into the epidermis eliminates the need of molecules to pass tortuous intercellular path within or through the stratum corneum in order to get into viable tissues. This has several implications:

The delivery of molecules occurs mainly through the micro-channels, which occupy less than 1% of the treated skin area.

There is no need to include penetration enhancers in the formulations.

Penetration enhancers disrupt the structure of the stratum corneum, and increase the solubility of molecules through the stratum corneum. However, as such they are responsible for undesired side effects like erythema, edema or pruritis. Elimination of penetration enhancers during micro-channel generation improves skin safety and achieves the desired cosmetic effect.

The delivery of molecules is efficient as the molecules reach the hydrophilic environment of viable tissues underneath the stratum corneum.

Based on these considerations, the system of the present invention is highly suitable for delivery of cosmetic agents through the new skin environment, which is created by ablation of the stratum corneum using electrical energy. As a consequence, the system of the present invention does not require the use of permeation enhancers for intradermal or transdermal delivery of cosmetic agents and is therefore not susceptible to the problems attendant therewith, particularly irritation.

The present invention integrates the devices and techniques for creating micro-channels by inducing ablation of the stratum corneum applying electrical current or spark generation disclosed in U.S. Pat. Nos. 6,148,232; 6,597,946; 6,611,706; 6,711,435; 6,708,060; and 6,615,079, incorporated herein in their entirety by reference. However, any method known in the art for generating channels in the skin of a subject may be used (see, for example, U.S. Pat. Nos. 5,885,211; 6,022,316; 6,142,939; and 6,173,202, incorporated herein in their entirety by reference).

According to one embodiment, the system of the present invention comprises an apparatus for facilitating intradermal or transdermal delivery of a cosmetic agent through skin of a subject, said apparatus comprising:

(i) an electrode cartridge comprising a plurality of electrodes;

(ii) a main unit comprising a control unit which is adapted to apply electrical energy between two or more electrodes when the electrodes are in vicinity of the skin, typically generating current flow or one or more sparks, enabling ablation of stratum corneum in an area beneath the electrodes, thereby generating at least one micro-channel.

According to another embodiment, the control unit of the apparatus comprises circuitry to control the magnitude, frequency, and/or duration of the electrical energy delivered to the electrodes, so as to control the current flow or spark generation, and thus the width, depth and shape of the one or more formed micro-channels. Preferably, the electrical energy is at radio frequency (RF).

The micro-channels formed by the apparatus of the present invention are hydrophilic, and typically have a diameter of about 10 to about 100 microns and a depth of about 20 to about 300 microns, thus facilitate the diffusion of substances through the skin.

According to the principles of the invention, the electrode cartridge comprises a plurality of electrodes thus forming an electrode array, which generates upon application of an electrical energy at least one micro-channel, and preferably a plurality of micro-channels, within the subject's skin. Typically, however, the overall area of micro-channels generated in the stratum corneum is small compared to the total area covered by the electrode array. It will be understood that the term "plurality" of electrodes refers herein to two or more electrodes.

According to a further embodiment, the pressure obtained while placing the apparatus of the present invention on a subject's skin activates the electrical energy delivered to the electrodes. Such mode of action ensures that activation of electrodes occurs only in a close contact with the skin enabling the desired formation of the micro-channels.

The number and dimension of micro-channels may be adjusted to the amount of the cosmetic agent desired to be delivered into the skin.

The electrode cartridge is preferably removable. According to certain embodiments, the electrode cartridge is discarded after one use, and as such is designed for easy attachment to the main unit and subsequent detachment from the main unit.

According to the present invention, micro-channels may be formed by the application of current to the skin in order to ablate the stratum corneum by heating the cells. Spark generation, cessation of spark generation, or a specific current level may be used as a form of feedback, which indicates that the desired depth has been reached and current application should be terminated. For these applications, the electrodes are preferably shaped and/or supported in a cartridge that is conducive to facilitate formation of micro-channels in the stratum corneum to the desired depth, but not beyond that depth. Alternatively, the current may be configured so as to form micro-channels in the stratum corneum without the generation of sparks. The resulted micro-channels are uniform in shape and size.

Thus, according to the present invention, the electrodes may be maintained either in contact with the skin, or in vicinity of the skin, up to a distance of about 500 microns therefrom. According to a further embodiment, ablation of the stratum corneum is performed by applying an electrical current having a frequency between about 10 kHz and 4000 kHz, preferably between about 10 kHz and 500 kHz, and more preferably at 100 kHz.

The cosmetic compositions of the invention comprise at least one water-soluble, poorly water-soluble, or water-insoluble cosmetic agent. According to another embodiment, the cosmetic agent is selected from xanthines, retinoids, α-hydroxy acids, β-hydroxy acids, α-2 adrenergic inhibitors, β-adrenergic agonists, aromatase inhibitors, anti-estrogens, hydroquinone, ascorbic acid, kojic acid, corticosteroids, mucopolysaccharides, collagen, estrogens, isoflavonoids, cinnamic acid, benzoyl peroxide, tropolone, catechol, mercaptoamine, niacinamide, tocopherol, ferulic acid, azelaic acid, botulinum, urea, a salt or derivative thereof. In a currently preferred embodiment, the cosmetic agent is selected from caffeine, salicylic acid, and hydroquinone.

The composition of the invention also encompasses derivatives of the cosmetic agents. As used herein, the term "derivative" refers to forms of the cosmetic agents of the invention that have been chemically modified to improve their stability and/or bioavailability for topical administration, including those modifications intended to reduce oxidation upon exposure to air and/or light, and those modifications intended to increase the solubility in aqueous solutions and/or emulsions.

The composition of the invention encompasses salts of the cosmetic agents. Salts of the cosmetic agents will be prepared from dermatologically or pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, and the like. Thus, organic bases such as mono-, di- and tri-alkyl and aryl amines (e.g. triethylamine, diisopropylamine, methylamine, dimethylamine and the like) and optionally substituted ethanolamines (e.g. ethanolamine, diethanolamine and the like) may be used according to the principles of the invention.

When the cosmetic agent is basic, salts may be prepared from pharmaceutically acceptable non-toxic acids, including inorganic and organic acids. Such acids include acetic, benzenesulfonic, benzoic, citric, ethanesulfonic, fumaric, gluconic, glutamic, hydrobromic, hydrochloric, isethionic, lactic, maleic, malic, mandelic, methanesulfonic, mucic, nitric, oxalic, pamoic, pantothenic, phosphoric, succinic, sulfuric, tartaric, p-toluenesulfonic acid, and the like.

The composition used in the invention may optionally comprise additional pharmaceutically acceptable safe active ingredients sufficiently high in purity and sufficiently low in toxicity to render them suitable for application to the skin of humans. Thus, according to the invention a cosmetic agent of the invention useful for treating a skin condition may be administered alone or in combination with at least one pharmaceutically active agent.

The compositions used in the present invention comprise a dermatologically acceptable carrier. The term "dermatologically acceptable carrier", as used herein, means that the carrier is suitable for topical application to the skin, has good aesthetic properties, is compatible with the cosmetic agents of the invention and the other ingredients in such a manner that there is no adverse interaction that would substantially reduce the efficacy of the composition during use. Examples of suitable carriers include, but are not limited to, squalene, olive oil, corn oil, canola oil, peanut oil, safflower oil, flax oil, sunflower oil, mineral oil, castor, cetyl alcohol, stearyl alcohol, and stearic acid, as well as water-based carriers as glycerin, water, alcohol, propylene glycol and the like.

The composition of the invention may be formulated in a variety of forms known to a person skilled in the art so as to increase the solubility of the cosmetic agents in the compositions and hence to improve their efficacy. These formulations include, but are not limited to, anhydrous compositions, aqueous solutions or suspensions, oil-in-water or water-in-oil emulsions such as macroemulsions, microemulsions or nanoemulsions, oily droplets in aqueous solutions, micelles, liposomes, ethosomes, or aqueous suspensions of nanoparticles (see, for example, U.S. Pat. Nos. 6,565,886 to Simonnet et al.; 6,562,356 to Verite et al.; 6,509,024 to Lorant; 5,599,533 to Stepniewski et al.; 5,202,126 to Perrier, et al., and Dayan, N. (2000) Biomaterials 21: 1879-1885, the contents of which are incorporated herein in their entirety by reference). The compositions may be in the form of a lotion, cream, ointment, paste, spray, foam, or any other form known in the art. Additionally, sticks or skin patches comprising the cosmetic agents of the invention may be used. The skin patches may be reservoir type transdermal patches where the agent is contained within a reservoir, matrix type transdermal patches where the agent is dispersed in a polymer layer, printed patches where the composition is dried or lyophilized, or any other patch known in the art for transdermal delivery of agents (see, for example, WO 2004/039426; WO 2004/039427; and WO 2004/039428, incorporated herein by reference as if fully set forth). The cosmetic agents contained within transdermal patches are typically more protected against air/light oxidation and/or degradation and thus are more stable.

Typically, the cosmetic compositions of the invention comprise other components including, but not limited to, surfactants, skin benefit materials such as humectants and emollients, preservatives, antioxidants, powders, clarifying agents, coloring agents, opacifiers, thickeners and perfumes as well known in the art.

Examples of moisturizers and humectants include polyols, urea, amino acids, glycerol, propylene glycol, cetyl alcohol, paraffin oils, lanolin and its derivatives, fatty acid esters, and the like. Silicone compounds such as silicone oil, cyclomethicones, dimethicones, dimethiconols may also be included.

Surfactants, which are also sometimes designated as emulsifiers, may be incorporated into the cosmetic compositions of the present invention. Surfactants may constitute anywhere from about 0.5% to about 30%, preferably from about 1% to about 15% by weight of the total composition. Surfactants may be cationic, nonionic, anionic, or amphoteric in nature and combinations thereof may be employed.

Emollients are also incorporated into cosmetic compositions. Levels of such emollients may range from about 0.5% to about 50%, preferably between about 5% and 30% by weight of the total composition. Emollients may be classified under general chemical categories as esters, fatty acids and alcohols, polyols and hydrocarbons.

Powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

According to another aspect, the present invention provides a method for treating a skin condition in a subject, said method comprising the steps of:
(i) generating at least one micro-channel in a region of skin of a subject suffering from a skin condition; and
(ii) topically applying a cosmetic or dermatological composition comprising a dermatologically effective amount of at least one water-soluble, poorly water-soluble, or water-insoluble cosmetic agent and a cosmetically or dermatologically acceptable carrier to the region of the skin in which the micro-channels are present so as to improve the skin condition of the subject.

The term "topically applying" refers to the delivery of a composition into the skin, through/across the stratum corneum. The term "local" when used in reference to a composition, refers to its function in a particular region. Thus, a composition of the invention topically applied to a region of the skin of a subject is believed to exert its dermatological or cosmetic activity within at least one layer, e.g., epidermis, dermis, subcutaneous layer, of the skin.

In accordance with the invention, a "dermatologically effective amount" of a composition delivered topically, e.g., through the stratum corneum, to a region of skin in which micro-channels are present, is an amount effective to produce a desired cosmetic and/or dermatological effect, such as preventing or inhibiting a degenerative skin condition or promoting skin healing so as to improve skin appearance in a subject in need thereof. The amount required for cosmetic or dermatological treatment will vary from subject to subject, depending on the gender, age, general condition of the subject (physiological and psychological), the severity of the condition being treated (e.g., chronic vs. acute), the anatomical region of the skin being treated, the type of formulation, and other factors known in the art.

According to the invention, the composition is administered topically to a region where micro-channels are present using the apparatus of the invention described herein above. However, the method for treating a skin condition in a subject may optionally further comprise additional steps that can increase the efficiency of topically introducing a composition of the invention into the skin. The steps may include mechanical or physical action, or any composition that increases the permeation of the composition of the invention.

According to the invention, the composition and the transdermal apparatus are applied to the region of skin to be treated reasonably close together in time. Preferably, the composition is administered after the generation of micro-channels. When applying multiple sparks, the composition can be administered before or after each of the sparks, or at any time between the sparks.

According to one embodiment, the subject is a human subject.

According to another embodiment, the skin condition that may be treated using the system of the invention includes, cellulite, acne vulgaris, acne cystic, skin aging, skin wrinkles, hyperpigmentation including discrete and mottled hyperpigmentation, keratosis including actinic, solar and sebhorratic keratosis, skin blemish, dandruff; warts, photodamaged skin, chronic dermatoses such as psoriasis, dermatitis including atopic dermatitis and seborrheic dermatitis, dryness, and other types of viral, fungal or bacterial skin infections.

Examples of skin conditions that may be treated by the methods of the present invention and examples of agents known in the art useful for treating these skin conditions are listed herein below. It will be understood that the present invention encompasses any and all of the agents listed herein below for treating any skin condition, particularly the skin conditions listed below.

Cellulite

Cellulite is characterized by thinning of the epidermal and dermal layers of the skin, the presence of subdermal agglomerations of fatty tissue surrounded by polymeric proteoglycans, accumulation of body fluids, degeneration of subcutaneous blood vessels, and poor blood flow. These effects result in an "orange peel" appearance of the skin. Cellulite is most commonly problematical on the thighs, buttocks and upper arms. While often associated with obesity, cellulite may also manifest itself in the skin of individuals of normal or near-normal weight.

Net fat removal from fatty tissue, which is constituted primarily of adipocytes, is dependent on a balance between the uptake of dietary triglycerides circulating in the blood via chylomicrons and the breakdown of stored triglyceride within the adipocyte. Lipolysis (breakdown of triglyceride within the adipocyte), occurs when the hormone sensitive lipase (HSL) is activated. HSL activation requires phosphorylation via a cyclic adenosine monophosphate (cAMP) dependent protein kinase. As such, cAMP level regulates lipolysis. Net level of cAMP is a result of a balance between its enzymatic synthesis from adenosine triphosphate (ATP) via adenylate cyclase and its breakdown via phosphodiesterases. Adipocytes express both β- and α-2 adrenergic receptors, which activate and inactivate, respectively, adenylate cyclase.

Most cellulite treatments focus on lipolysis as the primary mode of action. Soudant et al. (U.S. Pat. No. 5,194,259) teach anti-cellulite composition based on Ginko bilboa as an α-2 adrenergic blocker. The use of xanthines (e.g., caffeine) as phosphodiesterase inhibitors is also known for cellulite treatment. For instance, U.S. Pat. No. 5,215,759 to Mausner discloses anti-cellulite compositions based on a specific combination of five ingredients, which may further comprise methyl silanol elastimate, caffeine and methyl silanol theophillinacetate. U.S. Pat. No. 5,362,494 to Zysman et al., discloses cosmetic compositions containing, for example, xanthines as liporegulators, and hydroxy acids, in particular glycolic acid. Compositions containing xanthines and an inositol phosphoric acid and/or alpha hydroxy acid are described in U.S. Pat. No. 5,523,090 to Zaiden et al.

However, due to the limited solubility of some of the xanthines in water and their low skin penetration from typical cosmetic preparations (e.g., oil in water emulsion), xanthines in general, and caffeine in particular, have not had great success in the marketplace.

Other existing methods for treatment of cellulite involve the stimulation of adenylate cyclase so as to increase cAMP levels via β-adrenergic agonists. Greenway et al., (U.S. Pat. No. 4,588,724) disclose the use of isoproterenol, a β-adrenergic stimulator, or of a α-2 adrenergic inhibitor for accelerated reduction of a regional fat depots by stimulating lipolysis. Topically applied retinoids, as disclosed in U.S. Pat. No. 5,051,449 to Kligman, can retard and reverse cellulite. U.S. Pat. No. 6,071,526 to Schmidt et al., discloses aromatase inhibitors and anti-estrogens (for example, the non-steroid-type estrogen antagonists tamoxifen and aminoglutethimide) for topical administration in cosmetic treatment of cellulite. U.S. Pat. No. 5,962,482 to Bissett provides methods for treating cellulite using a skin care composition that comprises niacinamide.

Skin Whitening

Hyper-pigmentation in the skin is caused by the over expression or accumulation of melanin in the skin. One of the principal enzymes involved in melanin production is tyrosinase.

A variety of dermatological compositions have been suggested for skin whitening. Today, the only treatment for hyperpigmentation that is approved in the United States for use by consumers without a prescription is the topical application of hydroquinone, which acts by suppressing melanocyte activity. Hydroquinone is oxidized by air, light, and tyrosinase, each one of which adversely affect the shelf life of hydroquinone preparations and its bioavailability upon application. If applied over long periods of time, hydroquinone can cause serious side effects such as burning, redness, sensitization and irritation, which lead to its use at limited concentrations.

Better tolerated skin lightening substances currently being used are of natural origin, e.g., arbutin (from the leaves of the common bearberry, Uvae ursi), liquorice extract (from liquorice root), ascorbic acid (vitamin C from citrus fruits) and magnesium asccorbyl phosphate, and kojic acid (from carbohydrate solutions under the effect of certain bacteria). These substances act on tyrosinase as competitive inhibitors. However, there are many stability issues associated with these active agents when incorporated into aqueous systems. Both kojic acid and ascorbic acid are prone to oxidation in aqueous systems and have the disadvantage that only very small quantities penetrate the deeper skin layers and reach the melanocytes in the basal membrane. As a result high concentrations are required to achieve skin whitening effect. Compared to the quantity of hydroquinone used, 17 times as much ascorbic acid and over 100 times as much arbutin is required to achieve a similar effect.

Other dermatological compositions contain harsh chemicals such as peroxides, acids, formaldehydes, or thiolated materials such as glutathione, cysteine, mercaptosuccinic acid, mercaptodextran, and mercaptoethanol, which have an objectionable odor that makes products containing them undesirable to a consumer. Topical retinoids and topical corticosteroids have also been suggested as hypopigmenting agents, but these fall short of desirable responses.

In addition, compounds isolated from Aloe, particularly aloesin and one of its derivatives, 2"-O-feruloylaloesin, have been suggested as effective inhibitors of tyrosinase.

Combination therapies were also suggested to improve the bioavailability and stability of kojic acid, ascorbic acid, and hydroquinone (see, for example, U.S. Pat. No. 6,365,137 to Aust et al., and U.S. Pat. No. 6,417,226 to Perricone).

Anti-Aging

Aging of the skin resulting from the effects of intrinsic or extrinsic factors on the skin is reflected by the appearance of wrinkles and fine lines, by yellowing of the skin which develops a parchment-like appearance accompanied by the appearance of pigmentation blemishes, by the disorganization of the elastin and collagen fibers, causing a loss of elasticity, flexibility and firmness. Specific manifestations of skin aging are the cross-linking reaction of collagen and the reduction in hyaluronic acid and other mucopolysaccharides. Thus, in conventional cosmetic compositions, the effort had been focused upon maintaining skin moisture by blending in mucopolysaccharides or collagen and other biochemical and synthetic polymer products. However, these substances were found to be ineffective in preventing skin aging.

Various cosmetic compositions intended to combat aging of the skin are known. Thus, retinoic acid has been disclosed as anti-aging agent in cosmetic compositions, for example in U.S. Pat. No. 4,603,146. Retinoids have been shown to enhance keratinocyte proliferation in vitro, to increase epidermal thickness, and to increase collagen synthesis by dermal fibroblasts. These effects bring about smoothing of wrinkled skin.

α-Hydroxy acids such as lactic acid, malic acid, glycolic or alternatively citric acid are also known for this same application. These acids have been introduced into numerous cosmetic compositions on the market.

β-hydroxy acids, and specifically salicylic acid and derivatives thereof, are also known for this application (see, for example, U.S. Pat. No. 4,767,750).

All of these compounds act against aging of the skin by desquamation, i.e., removal of the dead cells located at the surface of the stratum corneum. Unfortunately, their use at high concentrations may occasionally be associated with skin irritation, e.g. skin redness and stinging sensation upon application. The irritation can be ameliorated by lowering the amount of the active ingredient in the composition or by reducing its penetration through the skin. A serious drawback of both approaches is that the efficacy is impaired.

The use of unsaturated fatty acids such as gamma linolenic acid (GLA) to reduce irritation of the skin by retinoids and/or hydroxy acids has been described (see, for example, U.S. Pat. Nos. 5,445,822 and 5,690,947).

Estrogen hormones have been also used for treating skin aging either in an oral form or as topical skin creams or gels. These treatments have produced augmented skin thickness, greater hydration, and improvements in elasticity and firmness. It is believed that the effectiveness of estrogen hormones is related to the increase in the amount of skin collagen, which is caused by stimulating collagen synthesis. Besides being able to increase skin collagen content, estrogen treatment also increases the content of elastic fibers, which improve the mechanical properties of skin. While estrogen can be used for treating and preventing skin aging, potential users of this hormone are concerned about the risk of side effects, particularly the increased risk of cancers of the breast and uterus. In addition, estrogen is typically not used in men, who also have problems with skin aging and wrinkles, because of the undesirable side effects of this female hormone in male users.

In order to overcome estrogen side effects, topical use of purified isoflavonoids, which are constituents of soy beans and other plants such as clover, was suggested so as to effectively treat and prevent symptoms of skin aging. These compounds are believed to have significant estrogenic activity, acting in the skin by stimulating the synthesis of collagen.

U.S. Pat. No. 5,352,438 to N'Guyen discloses cosmetic composition comprising a dismutase superoxide (DSO) in combination with a phosphonic acid. These compositions are suggested to be used in topical administration, in particular in the fight against skin aging and in the protection of skin against exposure to radiation.

U.S. Pat. No. 6,562,353 to Breton et al. discloses the use of cinnamic acid for combating skin aging. The cinnamic acid is believed to have fewer side effects than retinoids and hydroxy acids, while preserving their desquamation activity.

Other substances have been suggested for treating skin aging. For example, oligosaccharide derivatives were shown to inhibit elastase activity, and hence suggested to inhibit elastin degradation, a process that leads to skin aging (see, for example, U.S. Pat. No. 5,910,490 to Moczar et al.). Compositions comprising ubiquinones and plastoquinones as antioxidants have been also suggested (U.S. Pat. No. 5,889,062 to Hoppe et al.).

Acne

Aging, hormonal changes, and approaching adolescence often cause unsightly and embarrassing skin conditions which take the form of pimples, blemishes, pustules and reddened areas.

It is well known that puberty adversely affects the production of sebum, which in some cases is caused by increased levels of testosterone in both males and females. As testosterone level increases, it stimulates the sebaceous glands accompanying the hair follicles. In response, these glands become enlarged and begin to secrete more sebum than usual. In addition, testosterone causes the cells lining the skin pore to release more keratin, an insoluble protein that is the primary constituent of the hair and the epidermis. Together, the sebum and keratin block the skin pores, resulting in a comedones, also known as blackheads. Bacteria proliferate in the clogged pores, and the body typically responds by releasing enzymes to breakdown the sebum. Such enzymes cause the pore to become inflamed, a process that eventually may result in pustules or pimples. This condition is typically known as acne vulgaris. The response is especially prevalent on the face, back, and shoulders, where a greater amount of sebaceous glands exist.

Acne conglobate, more commonly known as nodular or cystic acne, is a more severe form of acne than acne vulgaris. In the case of nodular acne, the sebum builds up in the gland, mixes with dead cells, and eventually ruptures the follicle wall, which typically forms a deep cyst under the skin. Scarring often results from these deep cysts.

Non-vitamin methods of addressing acne commonly attempt to curb acne by mitigating the sebum production through drying agents. U.S. Pat. No. 4,536,399 to Flynn et al., describes a composition consisting essentially of benzoyl peroxide or salicylic acid and fumed silica intended to treat oily skin. Anti-acne compositions comprising benzoyl peroxide and irritation suppressants are described in U.S. Pat. No. 4,545,990 to Le Poyer de Costil et al. U.S. Pat. No. 4,608,370 to Aronsohn discloses a composition of salicylic acid, resorcinol, lactic acid and ethyl alcohol for light peeling of dead surface skin. U.S. Pat. No. 5,482,710 to Slavtcheff et al. discloses cosmetic compositions, which include at least one keratolytic agent (e.g., a combination of β- and α-hydroxy carboxylic acids such as salicylic acid and glycolic or lactic acid) and a combination of water-soluble and water insoluble anti-irritancy agents. Other anti-acne compositions are disclosed in U.S. Pat. No. 4,613,592 to Benzoni. These treatments utilize $C_1$-$C_4$ alkyl lactates as the active ingredient in a water-in-oil emulsion. Additionally, antibiotics, applied topically or orally, such as erythromycin, clindamycin, or tetracycline are commonly used to control bacterial growth. These treatments often lead to overly dry skin, and relapse is common after treatment has ended.

Vitamins and herbs often provide more promising results with regard to acne. U.S. Pat. No. 5,057,502 to Walsh disclose Juniper extract materials useful in thinning heavy oily, greasy skin secretions. Vitamin A has proven to be highly effective in treating acne. Since the early seventies, topical retinoic acid or tretinoin, both derivatives of vitamin A, have been used to treat acne topically. Co-actives to vitamin A, are reported to be aloe vera and camomile extract. Pulverized flowers are reported in the skin treatments of U.S. Pat. Nos. 4,880,621 and 4,933,177 to Grollier et al. Although many of the above-described treatment compositions and methods may prove useful, they suffer from slow performance and/or unsatisfactory results. In addition, some of these topical treatments tend to have side effects, which include stinging and reddening of the treated areas and possible photosensitivity.

A systemic vitamin A derivative for the treatment of nodular acne, known as isotretinoin, is commercially available under the name ACCUTANE®, from Roche Laboratories in Nutley, N.J. It has been found that treatment with isotretinoin can clear up as much as 85 percent of the acne over a 4 to 6 month period. Also, the patient's condition tends to improve even after the treatment has ceased. Unfortunately, side effects often result from the treatment with isotretinoin, and patients need to be monitored carefully.

Zinc is believed to be useful in the treatment of acne because of its ability to aid in wound healing, immune response, inflammation control, tissue regeneration, and more effective utilization of vitamin A. Certain studies have shown that zinc produces results similar to tetracycline in the treatment of superficial acne, but far superior results with regard to deeper forms of acne.

As skin disorders of the acne type concern impairment of both the surface layers of the skin, i.e., stratum corneum, and of the deeper layers of the epidermis and of the dermis, compositions and methods have been provided so as to simultaneously treat these skin layers. For example, U.S. Pat. No. 5,679,374 to Fanchon et al., discloses an anti-acne composition comprising a dispersion mixture of two lipid vesicles, the first are capable of penetrating into the deeper layers of the skin and contain active agent(s) such as anti-microbail agent, anti-inflammatory agent, or retinol, while the second are capable of penetrating into the stratum corneum and contain active agent(s) such as keratinolytic agents.

Accordingly, the compositions useful in providing cellulite control are exemplified, but are not limited to, phosphodiesterase inhibitors (e.g., xanthines), aromatase inhibitors (see, for example, U.S. Pat. No. 6,071,526, the content of which is incorporated herein by reference) and certain oleo-soluble vegetable extracts, including those of seaweed, climbing ivy (*Hedera helix*), arnica (*Arnica montana*), rosemary (*Rosmarinus officinalis* N), marigold (*Calendula officinalis*), sage (*Salvia officinalis* N), ginseng (*Panax ginseng*), St. Johns-wart (*Hypericum perforatum*), ruscus (*Ruscus aculeatus*), meadowsweet (*Filipendula ulmaria* L) and orthosiphon (*Ortosifon staminicus Benth*), as well as mixtures of these vegetable extracts, all of which are disclosed in U.S. Pat. No. 4,795,638, herein incorporated by reference.

The term "xanthines" as used herein includes, but is not limited to, the following compounds: xanthine; 1,3-dimethyl xanthine (commonly known as "theophylline"); 3,7-dimethyl xanthine (commonly known as "theobromine"); trimethyl xanthine (commonly known as "caffeine"); alloxantin; paraxanthine; heteroxanthine, derivatives and salts thereof.

Other anti-cellulite compositions that are known in the art and may be used according to the present invention are nicotinic acid, inositol hexanicotinate, lipid-degrading enzymes, α- or β-hydroxy acids, α-adrenergic inhibitors, β-adrenergic agonists, niacinamide and retinoids (see, for example, U.S. Pat. No. 5,051,449).

The term "retinoids" as used herein includes retinoic acid and derivatives thereof, such as retinol, retinal, retinyl acetate, tretinoin, and isotretinoin. Included in the term "retinoic acid" are 13-cis retinoic acid and all-trans retinoic acid. Thus, the present invention encompasses synthetic as well as natural products of retinoids.

Retinoids (e.g. Vitamin A and its derivatives) are known to have a broad spectrum of biological activity. More specifically, these substances affect cell growth, differentiation and proliferation. Vitamin A is essential for maintaining growth and differentiation of epithelial tissues. Retinoids act as a general growth stimulant to many kinds of cells found in skin and elsewhere. They stimulate fibroblasts to make collagen, the main constituent of the dermis. Retinoids induce formation of new blood vessels. The metabolic activity of other cell types is also increased. Retinoids have been extensively and effectively used to treat cellulite, acne vulgaris, hyperpigmentation, and a variety of chronic dermatoses, including psoriasis.

Thus, in a preferred embodiment, the cosmetic agent for treating cellulite is selected from xanthines, retinoids, and derivatives thereof. In a more preferred embodiment, the cosmetic agent is caffeine.

Hyperpigmentary skin conditions include, but are not limited to, freckles, melasma, cafe au lait, age and liver spots.

Tyrosinase inhibitors are known in the art for treating hyperpigmentation and causing skin whitening, and thus may be used as a cosmetic agent according to the invention (see, for example, U.S. Pat. No. 6,365,137). Tyrosinase inhibiting agents include, but are not limited to, kojic acid and its derivatives, glycyrrhetinic acid, glycyrrhizinic acid, hydroquinone and derivatives (e.g., arbutin), tyrosine, tyrosine derivatives, deoxyphenylalanine, dopaquinone, mimosine, benzhydroxamic acid, 2,3-dithiopropanol, tropolone, catechols, mercaptoamines, alpha hydroxy acids such as the monocarboxylic acids glycolic acid, mandelic acid, lactic acid, dicarboxylic acids (azelaic acid, sebacic acid), or mixtures thereof.

Thiolated materials such as mercaptosuccinic acid and mercaptoethanol have an objectionable odor that makes a composition comprising therewith undesirable to a consumer. Thiolated materials are also generally difficult to incorporate into water containing cosmetic formulations due to solubility difficulties. Thiolated materials are also encompassed in the present invention.

Other skin whitening agents that may be useful according to the invention include, but are not limited to, ascorbic acid, isoascorbic acid, dehydroascorbic acid, ascorbic acid phosphate, mono- or dialkyl derivatives of ascorbic acid or ascorbic acid phosphate such as ascorbyl palmitate, derivatives and mixtures thereof.

Other skin lightening agent, which may be chosen from any known such agent, are for example: niacin, niacinamide, placenta extract, ferulic acid, retinoids, organic sunscreens such as 4-tertiary butyl-4'-methoxy dibenzoylmethane, and/or 2-ethyl hexyl methoxyl cinnamate, inorganic sunscreens such as micronised titanium dioxide, zinc oxide or other UV A and UV B sunscreens and other known skin lightening compounds, all are encompassed in the invention.

Additionally, free radical scavengers or antioxidants may be added to the compositions of the invention. Free radical scavengers or antioxidants include, but are not limited to vitamin E, ubiquinones, superoxide dismutase, α-lipoic acid, Licorice extract, Rosemary extract and derivatives thereof. The mercaptodextran may also be combined with extracts or fermentates of acerola cherry.

Anti-aging (anti-wrinkling) compounds that may be used according to the present invention include, but are not limited to, α-hydroxy acids, retinoids and derivatives thereof, tocopherol and derivatives thereof, β-hydroxy acids and particularly salicylic acid and derivatives thereof, ubiquinones, cinnamic acid, mucopolysaccharides particularly hyaluronic acid, and botulinum.

Purified isoflavonoids may also be used according to the invention as anti-aging compounds and include genistein, daidzein, biochanin A, formononetin, O-desmethylangolensin, glycitin, and equol.

Numerous treatments, both topical and systemic, are currently employed for the treatment of acne (vulgaris and cystic) and may be useful for the present invention. Topical and systemic acne treatment compositions typically employ an active ingredient in combination with an acceptable carrier component. The active ingredients typically comprise an antibiotic/antibacterial such as tetracycline, erythromycin, clindamycin, and the like. Topical treatment compositions often include benzoyl peroxide in combination with the antibiotic and carrier in order to potentiate the effectiveness of the antibiotic. Thus, the compositions of the present invention may also comprise antibiotic/antibacterial agents.

The use of inositol phosphoric acid compounds in skin treatment compositions is also known, albeit to a much lesser extent and may be used in the present invention. U.S. Pat. No. 5,116,605 discloses compositions including phytic acid (also known as "inositol hexaphosphate") for mitigating acne.

Additional agents that may be used for treating acne according to the invention include, but are not limited to, azelaic acid, benzoyl peroxide, retinoic acid and derivatives thereof, salicylic acid, mandelic acid, alpha hydroxy acids, and zinc salts such as zinc cysteate, and zinc oxide.

It will be appreciated that the compositions of the present invention may further comprise anti-irritancy agents (see, for example, U.S. Pat. No. 5,482,710).

Having now generally described the invention, the same will be more readily understood through reference to the following examples, which are provided by way of illustration and are not intended to be limiting of the present invention.

EXAMPLES

The ViaDerm™ technology utilizes electrical current of radio frequency (RF) to create RF-MicroChannels™ through the outer layer of the skin. These micro-channels having precise dimensions enable controlled passage of molecules through and into the skin.

Instruments and Materials

In order to create micro-channels in porcine skin ViaDerm technology was used. The ViaDerm device disclosed in U.S. Pat. No. 6,148,232 and various improvements to this invention disclosed in U.S. Pat. Nos. 6,597,946; 6,611,706; 6,711,435; 6,708,060; 6,615,079 and in WO 2004/039426; WO 2004/039427; and WO 2004/039428, are referred herein by the term ViaDerm.

In brief, ViaDerm contains the following components:
1. A reusable main unit comprising a control unit, which generates an RF electrical current.
2. A disposable electrode cartridge comprising an array of microelectrodes attached onto the end of the main unit.

The density of the microelectrode array was 100 microelectrodes/cm$^2$. The ViaDerm was applied twice on each location, so that the density of the micro-channels was 200/cm$^2$. The skin was treated with an applied voltage of 330 V, frequency of 100 kHz, and five bursts.

In Vitro Skin Permeation Study

The permeability of the cosmetic agents through porcine skin was measured in vitro with a flow-through Franz diffusion cell system (Laboratory Glass Apparatus, Berkeley, Calif.). The diffusion area was 1 cm$^2$. Dermatomized (300-500 µm, Electric Dermatom, Padgett Instruments Ltd, Kansas, Mich., USA) porcine skin was excised from slaughtered white pigs (breeding of Landres and Large White, locally grown in Kibbutz Lahav, Israel). Transepidermal water loss, measurements (TEWL, Dermalab Cortex Technology, Hadsund, Denmark) were performed and only skin pieces with TEWL levels less than 15 g/m$^2$/h were mounted in the diffusion cells. Skin micro-channeling was performed in cells defined as VD (ViaDerm) application group, and then TEWL was measured again to control the operation. The skin pieces were placed on the receiver chambers with the stratum corneum facing upwards, and the donor chambers were clamped in place. Phosphate buffered saline (PBS, pH 7.4 or pH 5.5) or 1% Volpo S-20 in PBS were passed through the acceptor cells at a flow rate of 3 ml/hr. Samples from the acceptor solutions were collected into tubes (using a fraction collector, Retriever IV, ISCO, Lincoln, Nebr., USA) at predetermined times for up to 24 hr period. The samples were kept at 4° C. until analyzed by HPLC.

Assay of the Cosmetic Agents by HPLC

Samples from the acceptor solutions (10-50 µl) were injected into HPLC system (Waters) equipped with a pre-packed LiChrospher C$_{18}$ column (150×3.9 mm, 5 µm; Waters), and a UV detector. The caffeine samples were separated using an isocratic mobile phase containing 30% methanol and 0.2% H$_3$PO$_4$ in H$_2$O, at a flow rate 1 ml/min. The detection of caffeine was performed at a wavelength of 280 nm.

The Salicylic acid samples were separated using an isocratic mobile phase containing 5% methanol 25% Acetonitrile and 0.01 mol/l $KH_2PO_4/H_3PO_4$ buffer pH 2.3 in $H_2O$, at a flow rate 1 ml/min. The detection of salicylic acid was performed at a wavelength of 237 nm.

The hydroquinone samples were separated using an isocratic mobile phase containing 20% methanol 80% $H_2O$, at a flow rate 0.12 ml/min. The detection of hydroquinone was performed at a wavelength of 280 nm.

Example 1

In Vitro Permeation Study of Caffeine

The cumulative permeability and permeation efficacy of caffeine from an aqueous solution or from commercially cosmetic gels through ViaDerm treated porcine skin or through intact porcine skin was evaluated. The permeation efficacy is defined as the % of penetrated agent out of total amount of the agent applied on the skin.

Caffeine Solution

The permeation of caffeine from caffeine solution through ViaDerm treated porcine skin was compared to that of intact skin.

Caffeine was purchased from Sigma. Caffeine solution (0.25 ml of 1% w/v) was pipetted into the donor chambers.

FIG. 1 shows the caffeine cumulative permeability through ViaDerm treated porcine shin compared to intact skin. As shown in FIG. 1, skin cumulative permeability of caffeine was enhanced following pretreatment with the ViaDerm in comparison to untreated control skin.

Caffeine flux through pretreated skin reached a plateau of 18.5±2.2 μg/ml after 6 hours in comparison to 0.4±0.3 μg/ml obtained in control untreated skin group. The permeation efficacy of caffeine using the ViaDerm technology was 10 fold higher in comparison to the untreated skin after 16 hours (37.1±4.8 versus 3.6±2.6% for pretreated and untreated skin, respectively).

Caffeine from Commercial Product #1

In order to evaluate the permeation of caffeine from a cosmetic gel through ViaDerm treated porcine skin, a commercial product of L'Oreal, "L'Oreal Plenitude: Perfect Slim-gel" designated herein commercial product #1, was used. The gel (4 mg, 3% caffeine content) was spread on porcine skin pieces using a plastic cup. The plastic cup was weighted before and after the gel spreading to determine the amount of gel spread.

Figure 2:
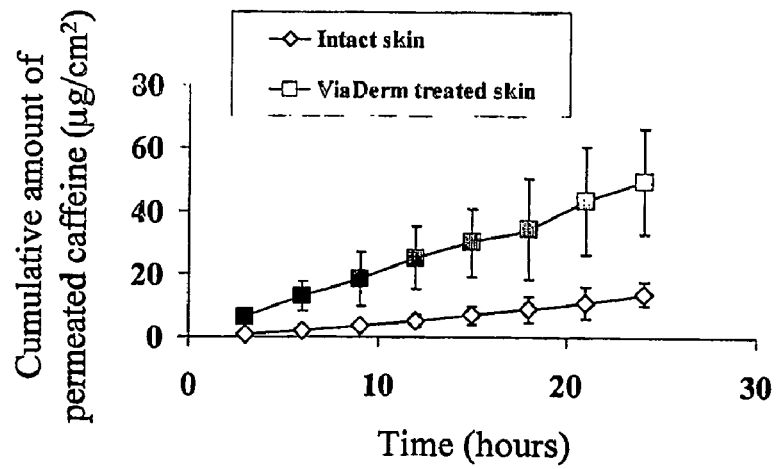
FIG. 2 shows permeation assay of caffeine from a commercial gel designated commercial product #1 through porcine ear skin in which skin micro-channels were generated compared to intact skin.

FIG. 2 shows the cumulative permeability of caffeine from commercial product #1 through ViaDerm treated porcine skin compared to intact skin. As shown in FIG. 2, the cumulative permeability of caffeine from commercial product #1 through ViaDerm treated skin was higher than through intact skin.

The permeation efficacy of caffeine from commercial product #1 was determined in ViaDerm treated skin and in intact skin.

TABLE 1

Permeation efficacy of caffeine present in commercial product #1.

| | Permeation Efficacy (%) - product #1 | | |
|---|---|---|---|
| Time (hr) | Intact Skin | VD Treated Skin | VD/intact ratio |
| 3 | 0.57 ± 0.40 | 5.21 ± 1.58 | 9.21 |
| 6 | 1.70 ± 0.36 | 11.01 ± 3.36 | 6.47 |
| 9 | 3.08 ± 0.81 | 15.47 ± 6.12 | 5.03 |
| 12 | 4.42 ± 1.45 | 20.41 ± 6.44 | 4.62 |
| 15 | 5.89 ± 2.21 | 25.51 ± 7.98 | 4.33 |
| 18 | 7.45 ± 3.05 | 29.17 ± 11.87 | 3.92 |
| 21 | 9.11 ± 3.84 | 35.42 ± 11.39 | 3.89 |
| 24 | 11.68 ± 2.61 | 40.88 ± 11.48 | 3.50 |

Table 1 shows that the permeation efficacy of caffeine from commercial product #1 was 9.2 and 3.5 times higher in ViaDerm treated skin than in control intact skin after 3 and 24 hours, respectively. These results demonstrate a novel way to enhance the delivery of caffeine from a commercial gel.

The in-vitro skin permeation of caffeine from commercial product #1 through porcine skin was also evaluated as a function of the gel amounts.

Commercial product #1 (3% caffeine content) was spread at various gel amounts: 2, 10, 30, and 50 mg on porcine skin pieces as described herein above. The flow rate of PBS through the receiver cells was 0.9 ml/hour.

Figure 3:
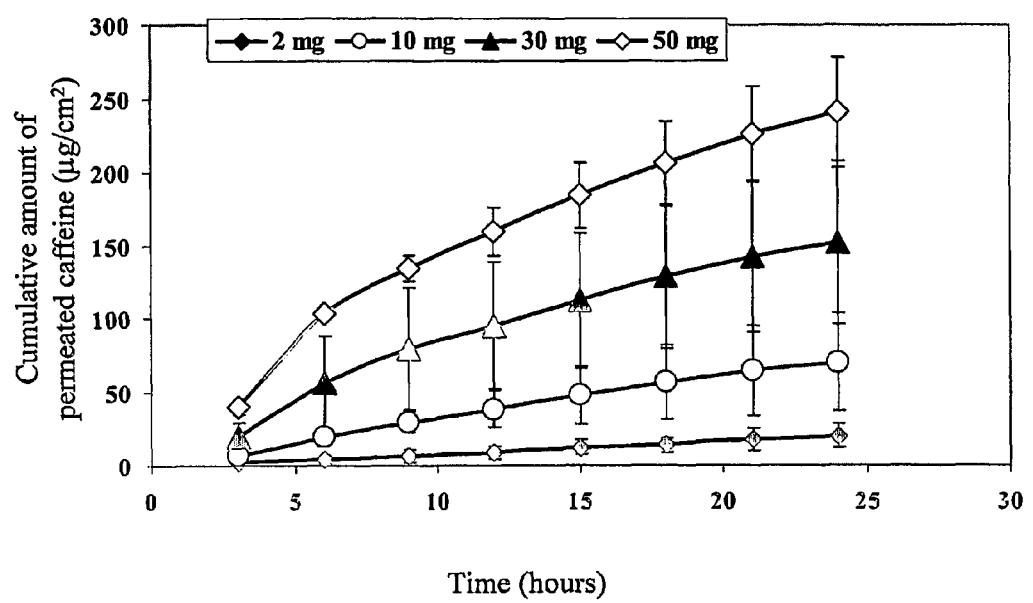
FIG. 3 shows permeation assay of caffeine from a commercial gel designated commercial product #1 through porcine ear skin in which skin micro-channels were generated. The permeation of caffeine was measured as a function of the amount of gel applied.

FIG. 3 shows the cumulative skin permeability of caffeine from commercial product #1 as a function of the amount of gel applied. As shown in FIG. 3, the cumulative skin permeability of caffeine from commercial product #1 increased when the gel amount was increased (20.1±8.7, 70.2±33.6, 152.0±55.7, and 241.0±37.7 μg/$cm^2$ after 24 hr when 2, 10, 30 and 50 mg, respectively, of gel were applied). However, the permeation efficacy of caffeine was decreased with the increase in the gel amount (32.2±15.9, 23.4±11.2, 16.9±6.2, and 16.1±2.5% for 2, 10, 30, and 50 mg of gel, respectively).

Caffeine from Commercial Product #2

In order to confirm the results that skin permeability and permeation efficacy of caffeine from commercial product #1 are applicable to caffeine from other gel formulations, in vitro permeability assay of caffeine from Roc's "Retinol Anti-Cellulite", designated herein commercial product #2, was performed.

Commercial product #2 (4 mg, 1.5% caffeine content) was spread on porcine skin pieces using a plastic cup. The plastic cup was weighted before and after the gel spreading to determine the amount of gel spread. The permeation of caffeine from the commercial product #2 through ViaDerm treated skin was compared to that of intact skin.

Figure 4:
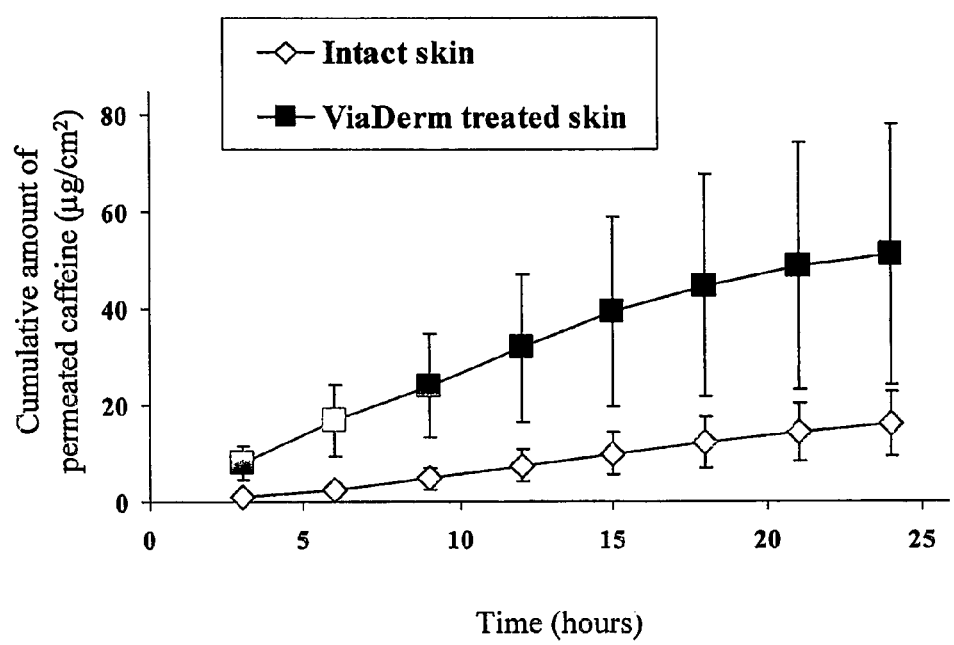
FIG. 4 shows permeation assay of caffeine from a commercial gel designated commercial product #2 through porcine ear skin in which skin micro-channels were generated compared to intact skin.

FIG. 4 shows the cumulative permeability of caffeine from commercial product #2 through ViaDerm treated skin and through intact skin. As shown in FIG. 4, the cumulative permeability of caffeine from commercial product #2 through ViaDerm treated skin was higher than through intact skin. The permeation efficacy in ViaDerm treated skin was 7.7 and 2.9 times higher than in control intact skin after 3 and 24 hours, respectively (see Table 2). It should be noted that the permeation efficacy of caffeine through ViaDerm treated skin was very high (79% after 24 hours, see Table 2).

TABLE 2

Permeation efficacy of caffeine present in commercial product #2

| | Permeation Efficacy (%) - product #2 | | |
|---|---|---|---|
| Time (hr) | Intact Skin | VD Treated Skin | VD/intact ratio |
| 3 | 1.60 ± 1.03 | 12.36 ± 4.10 | 7.72 |
| 6 | 4.40 ± 2.42 | 26.04 ± 7.76 | 5.92 |

TABLE 2-continued

Permeation efficacy of caffeine present in commercial product #2

| | Permeation Efficacy (%) - product #2 | | |
|---|---|---|---|
| Time (hr) | Intact Skin | VD Treated Skin | VD/intact ratio |
| 9 | 7.99 ± 4.06 | 36.89 ± 11.38 | 4.62 |
| 12 | 12.48 ± 5.61 | 49.06 ± 17.69 | 3.93 |
| 15 | 16.85 ± 7.29 | 60.35 ± 24.08 | 3.58 |
| 18 | 20.84 ± 8.72 | 69.01 ± 28.96 | 3.31 |
| 21 | 24.25 ± 9.91 | 75.37 ± 32.74 | 3.11 |
| 24 | 27.03 ± 10.90 | 79.12 ± 34.56 | 2.93 |

These results with caffeine in solution, caffeine in commercial product #1, and caffeine in commercial product #2 (Example 4 herein above) indicate that the transdermal delivery of caffeine from a solution or from a commercial gel is enhanced using ViaDerm technology that generates micro channels in skin.

Example 2

In Vitro Skin Permeation Study of Salicylic Acid

Salicylic Acid in Solution

Salicylic acid was obtained from Carlo Erba (Milan, Italy). Salicylic acid solution (0.25 ml of 0.5% w/v in PBS containing 10% ethanol) was freshly prepared and pipetted into the donor chambers. Acceptor medium for the diffusion chambers was 1% Volpo S-20 (Croda; North Humberside, England) in PBS.

Figure 5:
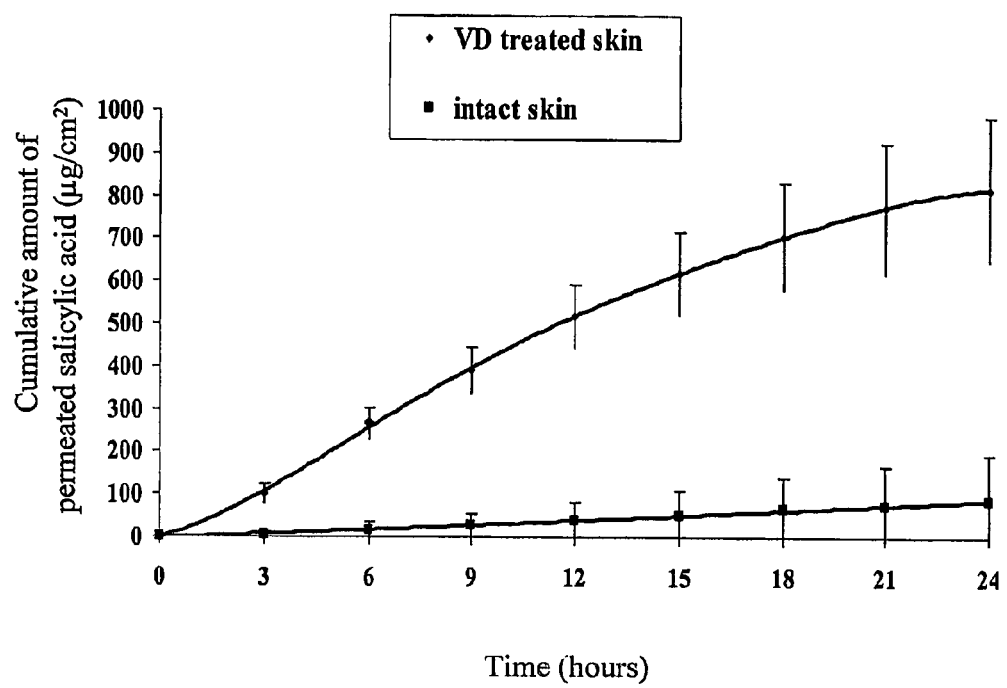
FIG. 5 shows permeation assay of salicylic acid from an aqueous solution through porcine ear skin in which skin micro-channels were generated compared to intact skin. VD denotes ViaDerm.

The permeation of salicylic acid from salicylic acid solution through ViaDerm treated skin was compared to that of intact skin.
The skin permeability of salicylic acid from salicylic acid solution was enhanced following pretreatment with ViaDerm in comparison to the permeability of the untreated control skin (FIG. 5). The total permeated amount after 24 hr in ViaDerm treated skin was 820 µg/cm$^2$ in comparison to 84 µg/cm$^2$ obtained for the control untreated skin group. The permeation efficacy was 62% and 4% in ViaDerm treated and untreated skin after 24 h, respectively. The differences in the permeated amount decreased in time (e.g., 17 and 10 fold higher in ViaDerm treated compared to untreated skin after 3 and 24 h, respectively).

Salicylic Acid from Commercial Product #3

In order to evaluate the permeation of salicylic acid from a cream, L'Oreal cream, designated commercial product #3, was spread (4 mg, 0.2% salicylic content) on the skin using a plastic cup. The plastic cup was weighted before and after the spreading to guarantee the desired weight. The permeation of salicylic acid from the cream through ViaDerm treated skin was evaluated and compared to that of intact skin.

Figure 6:
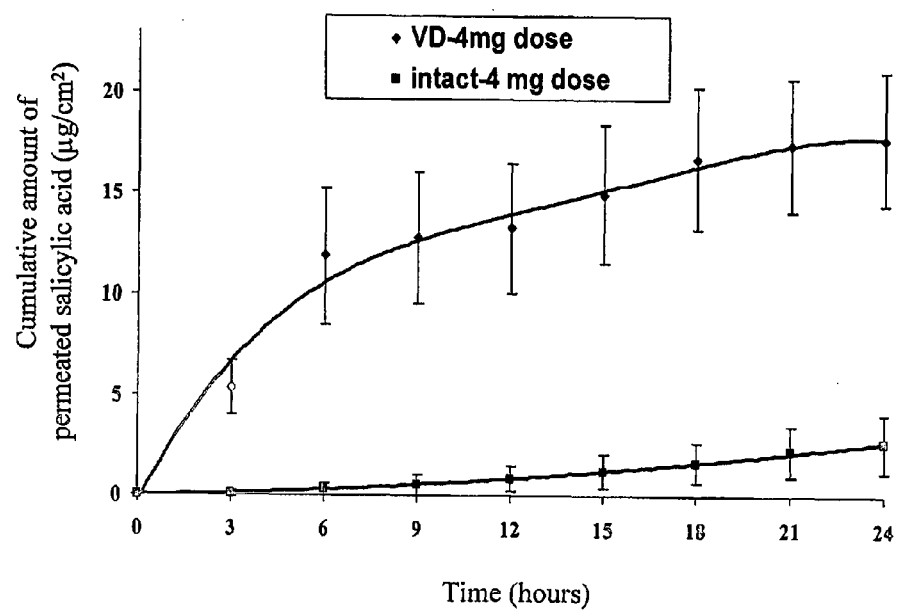
FIG. 6 shows permeation assay of salicylic acid from a commercial gel designated commercial product #3 through porcine ear skin in which skin micro-channels were generated compared to intact skin. VD denotes ViaDerm.

The skin permeability of salicylic acid from commercial product #3 was enhanced following pretreatment with ViaDerm in comparison to the permeability of the untreated control skin (FIG. 6). The total permeated amount after 24 hr in ViaDerm treated skin was 17.8±3.3 µg/cm$^2$ in comparison to 2.6±1.4 µg/cm$^2$ obtained for the control untreated skin group. The permeation efficacy was 90% and 13% for the ViaDerm treated and untreated skin after 24 h, respectively. The differences in the permeated amount were very high in the first hours and decreased with time (e.g., 51, 16 and 7 fold higher in comparison to the untreated skin after 3, 12 and 24 h, respectively).

Example 3

In Vitro Skin Permeation of Hydroquinone

Hydroquinone in Solution

Hydroquinone was obtained from Aldrich (Germany). Hydroquinone solution at a concentration of 2% in PBS was freshly prepared. Acceptor medium for the diffusion chambers was PBS at pH=7.4.

Hydroquinone solution (0.25 ml of 2% w/v) was pipetted into the donor chambers. The permeation of the hydroquinone solution through ViaDerm treated skin was compared to that of intact skin.

Figure 7:
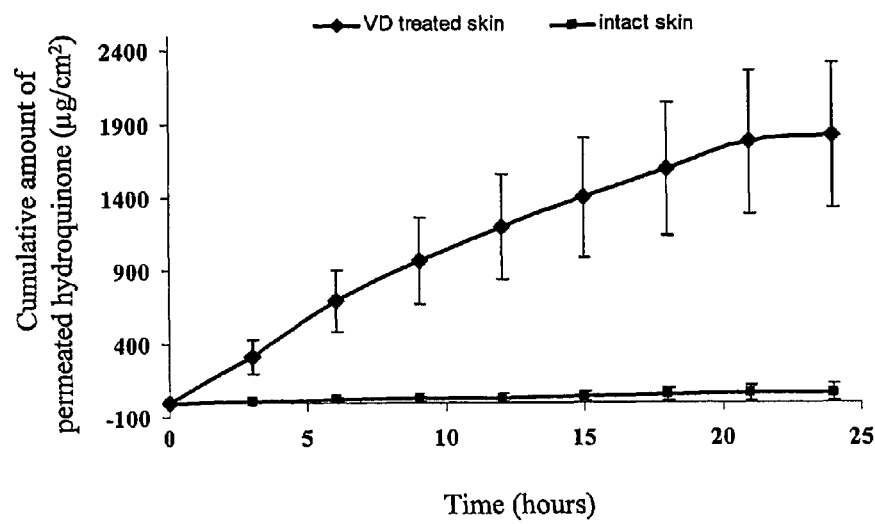
FIG. 7 shows permeation assay of hydroquinone from an aqueous solution through porcine ear skin in which skin micro-channels were generated compared to intact skin. VD denotes ViaDerm.

The skin permeability of hydroquinone solution was enhanced following pretreatment with ViaDerm in comparison to the permeability of the untreated control skin (FIG. 7). The total permeated amount after 24 hr in ViaDerm treated skin was 1824 µg/cm$^2$ in comparison to 62 µg/cm$^2$ obtained for the control untreated skin group. The permeation efficacy was 27% and 1% in ViaDerm treated skin and untreated skin after 24 h, respectively. The differences in the permeated amount decreased with time and were between 39 (at 3 hr time point) to 29 fold higher (at 24 hr time point) for the ViaDerm treated skin group in comparison to the untreated skin group.

Hydroquinone in Commercial Product #4

In order to evaluate the permeation of hydroquinone from a cream, Medibrands "Esomed neck & hand cream", designated commercial product #4, was spread (4 mg, 2% hydroquinone content) on the skin using a plastic cup. The plastic cup was weighted before and after the spreading to guarantee the desired weight. The permeation of hydroquinone from the cream through ViaDerm treated skin was compared to that of intact skin. Acceptor medium for the diffusion chambers was PBS at pH=5.

Figure 8:
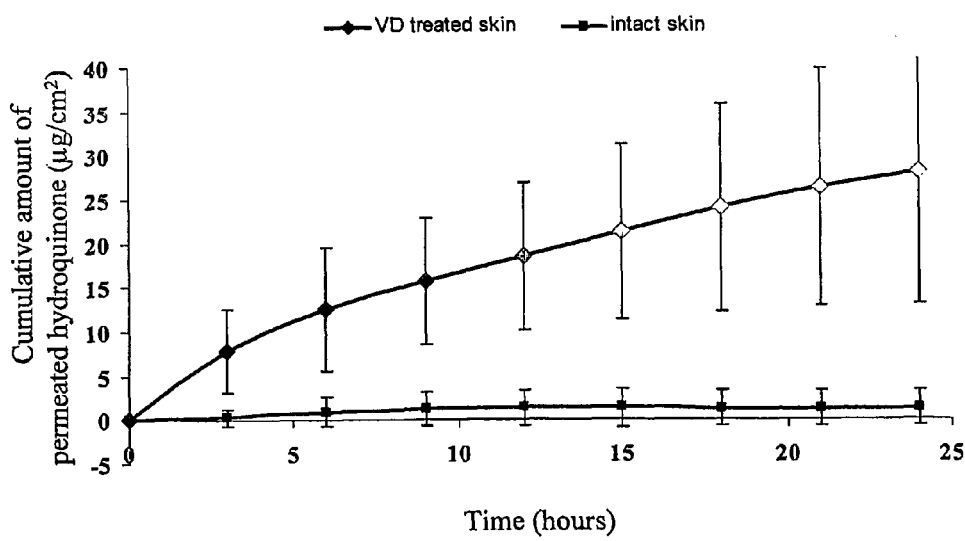
FIG. 8 shows permeation assay of hydroquinone from a commercial gel designated commercial product #4 through porcine ear skin in which skin micro-channels were generated compared to intact skin. VD denotes ViaDerm.
Figure 9:
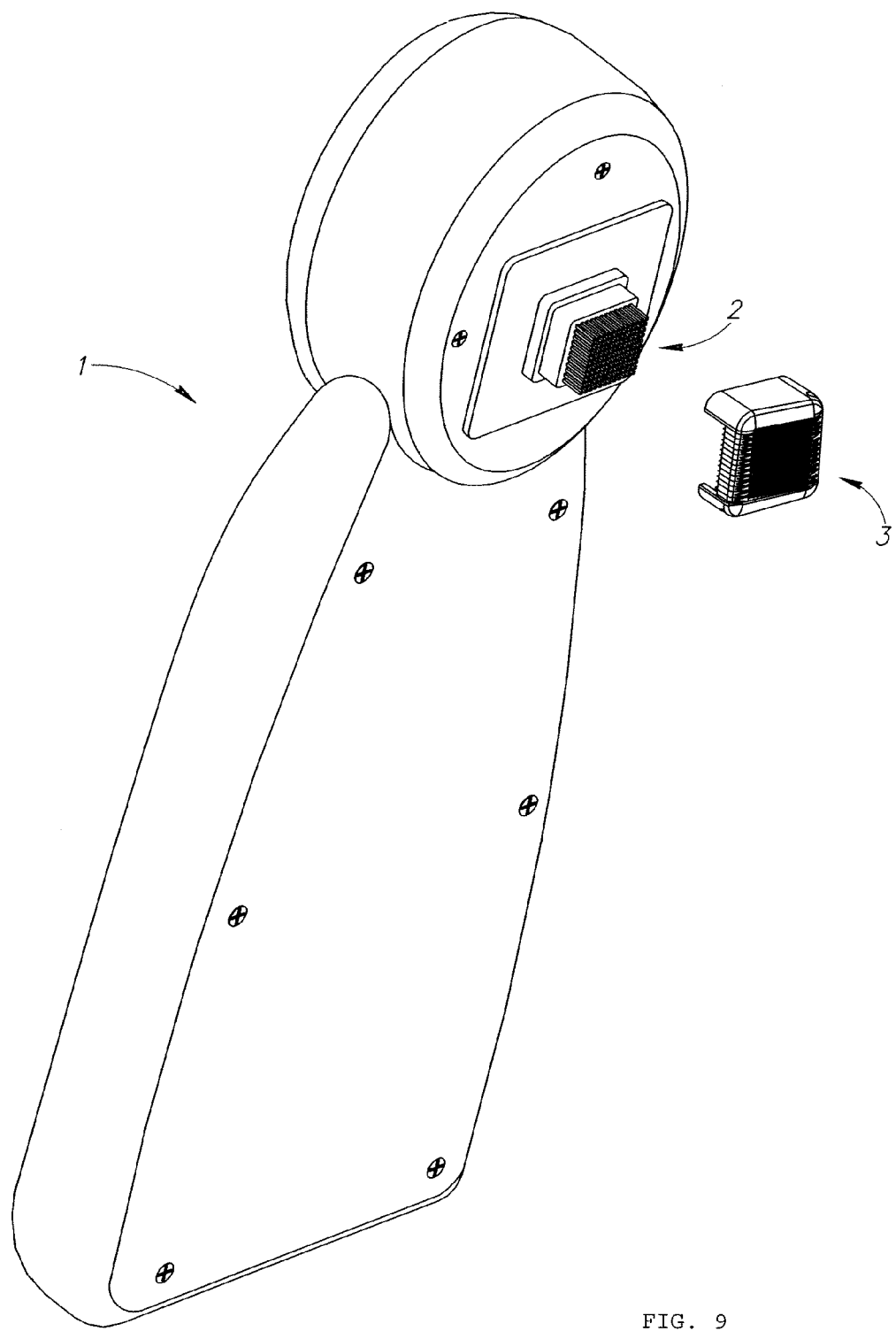
FIG. 9 shows the apparatus with the main unit (1) which contains electrical contacts (2) through which the electrical energy from the main unit is transferred to the electrode cartridge (3).
Figure 10:
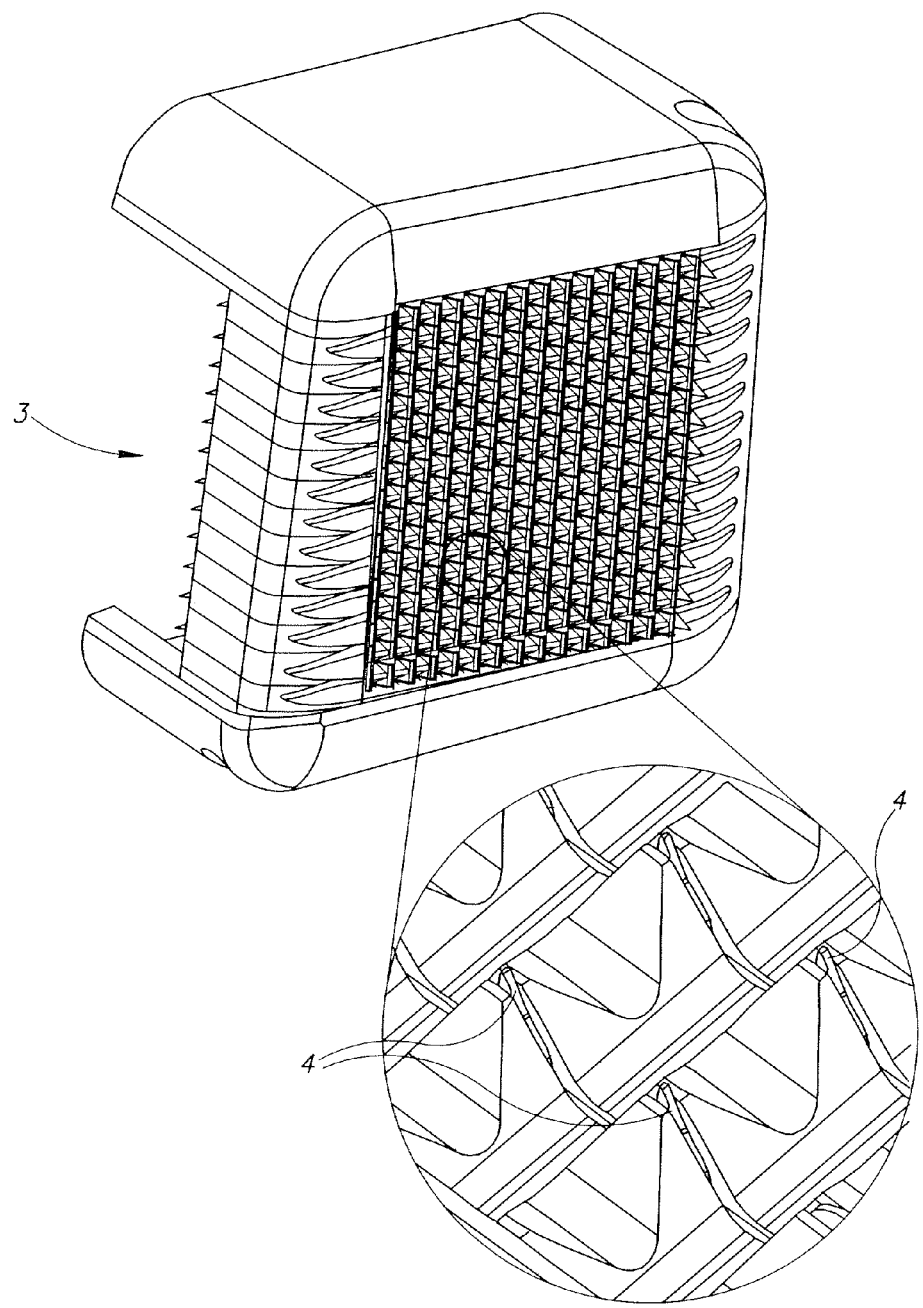
FIG. 10 is an enlarged view of a region of the electrode cartridge (3) showing the electrodes (4).

The skin permeability of hydroquinone from the cream was enhanced following pretreatment with the ViaDerm in comparison to the permeability of the untreated control skin (FIG. 8). The total permeated amount after 24 hr in ViaDerm treated skin was 28 µg/cm$^2$ in comparison to 1.4 µg/cm$^2$ obtained for the control untreated skin group. The permeation efficacy in ViaDerm treated skin was 35% vs. 2% in untreated skin after 24 h. The differences in the permeated amount changed between 12 (at 6 hr) to 20 (at 24 hr) fold higher for the micro-channeled group in comparison to the untreated skin group.

Enhanced transdermal delivery of cosmetic agents such as salicylic acid and hydroquinone from a solution or a commercial cream was demonstrated using the ViaDerm technology. The skin permeation through ViaDerm treated skin was much higher than its permeation through intact skin. The ViaDerm technology achieves high permeation rate and high permeation efficacy of salicylic and hyroquinone.

Example 5

The Performance of ViaDerm Apparatus In Vivo

Histological studies of micro-channels formed by ViaDerm in a porcine skin showed that the dimensions of the micro-channels are controllable and precise: each micro-channel was 30 µm in width and 50-100 µm in depth. In porcine skin, where the epidermis depth is about 40 µm, these micro-channels penetrated into the dermis. However in humans, where the epidermis depth is about 100 µm, such micro-channels reside within the limits of the epidermis. The micro-channels were very localized, and the skin surrounding the micro-channels maintained its normal structure.

Transepidermal water loss (TEWL) was measured in skin sections of porcine ear after generating different numbers of micro-channels. TEWL linearly increased with increasing number of micro-channels.

It will be appreciated by persons skilled in the art that the present invention is not limited by what has been particularly shown and described herein above. Rather the scope of the invention is defined by the claims that follow.

The invention claimed is:

1. A method for treating a skin condition in a subject comprising the steps of:
   (i) pretreating skin by generating a plurality of micro-channels in an area of skin of a subject suffering from a skin condition by an apparatus which comprises:
      a. an electrode cartridge comprising a plurality of electrodes to be oriented generally perpendicularly to the skin with electrode ends in the vicinity of the skin; and
      b. a main unit comprising a control unit which is adapted to apply electrical energy between two or more electrodes when the electrodes are in vicinity of the skin, typically generating current flow that passes between the electrodes and through the stratum corneum, enabling ablation of stratum corneum in the area beneath the electrodes, thereby generating in the stratum corneum a plurality of micro-channels having a diameter of about 10 microns to about 100 microns and a depth of about 20 microns to about 300 microns; and
   (ii) topically applying to the pre-treated skin and without the application of mechanical or physical means that increases the permeation of the composition through the skin a dermatologically effective amount of a cosmetic or dermatological composition comprising at least one water-soluble, poorly water-soluble or water-insoluble cosmetic agent and a cosmetically or dermatologically acceptable carrier to the area of the skin in which the micro-channels are present so as to improve the skin condition of said subject, the cosmetic or dermatological composition is devoid of permeation enhancers, wherein the electrode cartridge is configured and dimensioned for removable attachment to the main unit wherein the cartridge is removably attached to the main unit for applying the electrical energy and thereafter can be detached.

2. The method according to claim 1, wherein the cosmetic agent is selected from the group consisting of xanthines, retinoids, α-hydroxy acids, β-hydroxy acids, α-2 adrenergic inhibitors, β-adrenergic agonists, aromatase inhibitors, anti-estrogens, hydroquinone, ascorbic acid, kojic acid, corticosteroids, mucopolysaccharides, collagen, estrogens, isoflavonoids, cinnamic acid, benzoyl peroxide, tropolone, catechol, mercaptoamine, niacinamide, tocopherol, ferulic acid, azelaic acid, botulinum, urea, a derivative or salt thereof.

3. The method of claim 2, wherein the xanthine is caffeine.

4. The method according to claim 2, wherein the β-hydroxy acid is salicylic acid.

5. The method according to claim 2, wherein the cosmetic agent is hydroquinone.

6. The system according to claim 1, wherein the cosmetic or dermatological composition further comprises at least one component selected from the group consisting of surfactants, humectants, preservatives, antioxidants, powders, clarifying agents, coloring agents, opacifiers, thickeners, and perfumes, and the electrode cartridge is discarded after detachment from the main unit.

7. The method according to claim 1, wherein the cosmetic or dermatological composition further comprising a pharmaceutical agent.

8. The method according to claim 7, wherein the pharmaceutical agent is an antibacterial agent.

9. The method according to claim 1, wherein the cosmetic or dermatological composition is formulated in a form selected from the group consisting of anhydrous compositions, aqueous solutions, aqueous suspensions, oil-in-water emulsions, water-in-oil emulsions, oily droplets in aqueous solutions, micelles, liposomes, ethosomes, and aqueous suspensions of nanoparticles.

10. The method according to claim 1, wherein the cosmetic or dermatological composition is in a form selected from the group consisting of lotions, creams, ointments, gels, pastes, sprays, foams, sticks, and skin patches.

11. The method according to claim 1, wherein the skin condition is selected from cellulite, acne vulgaris, acne cystic, skin aging, skin wrinkles, hyperpigmentation, keratosis, skin blemish, dandruff, warts, photodamaged skin, chronic dermatoses, dermatitis, dryness, ichthyosis, viral infections, fungal infections, and bacterial skin infections.

* * * * *